US008649983B2

(12) United States Patent
Rath et al.

(10) Patent No.: US 8,649,983 B2
(45) Date of Patent: Feb. 11, 2014

(54) METHOD FOR CELL IDENTIFICATION AND CELL SORTING

(75) Inventors: Detlef Rath, Neustadt (DE); Wilfried Kues, Neustadt (DE); Ulrike Taylor, Neustadt (DE); Stephan Barcikowski, Hannover (DE); Svea Petersen, Rostock (DE)

(73) Assignee: Masterrind, GmbH, Verden (DE)

( * ) Notice: Subject to any disclaimer, the term of this patent is extended or adjusted under 35 U.S.C. 154(b) by 26 days.

(21) Appl. No.: 13/003,962

(22) PCT Filed: Jul. 15, 2009

(86) PCT No.: PCT/EP2009/059117
§ 371 (c)(1),
(2), (4) Date: Mar. 31, 2011

(87) PCT Pub. No.: WO2010/007118
PCT Pub. Date: Jan. 21, 2010

(65) Prior Publication Data
US 2012/0094352 A1    Apr. 19, 2012

(30) Foreign Application Priority Data

Jul. 15, 2008  (DE) .......................... 10 2008 033 070
Jul. 17, 2008  (DE) .......................... 10 2008 033 570

(51) Int. Cl.
G06F 19/00    (2011.01)
C12Q 1/68     (2006.01)
C12N 15/11    (2006.01)

(52) U.S. Cl.
USPC ......... 702/20; 435/6.1; 536/24.31; 536/25.32

(58) Field of Classification Search
None
See application file for complete search history.

(56) References Cited

U.S. PATENT DOCUMENTS 5,840,504 A      11/1998  Blecher
2010/0311059 A1*  12/2010  Didion et al. ................. 435/6

FOREIGN PATENT DOCUMENTS

CA    1312565    *  1/1993  ............... C12Q 1/68
EP    0235046       9/1987

OTHER PUBLICATIONS

Thaxton et al. Gold nanoparticle probes for the detection of nucleic acid targets. Clinica Chimica Acta vol. 363, pp. 120-126 (2006).*
Tyagi et al. Molecular Beacons: Probes that Fluoresce upon Hybridization. Nature Biiotechnology vol. 14, pp. 303-308 (1996).*
Pellestor in situ aneuploidy assessment in human sperm: the use of primed in situ and peptide nucleic acid-fluorescence in situ hybridization techniques. Asian Journal of Andrology vol. 8,pp. 387-392 (2006).*
Xi et al. Use of DNA and Peptide Nucleic Acid Molecular Beacons for Detection and Quantification of rRNA in solution and in Whole Cells. Applied and Environmental Micribiology vol. 69, pp. 5673-5678 (2003).*
Chakrabarti et al. Nanocrystals Modified with Peptide Nucleic Acids (PNAs) for Selective Self-Assembly and DNA Detection. Journal of the American Chemical Society vol. 125, pp. 12531-12540 (2003).*
Dubertret et al. Single-mismatch detection using gold-quenched fluorescent oligonucleotides Nature Biotechnology vol. 19, pp. 365-370 (2001).*
Keij et al. High-Speed Photodamage Cell Selection Using a Frequency-Doubled Argon Ion Laser Cytometry vol. 19, pp. 209- 216 (1995).*
Johnson Sex Preselection by Flow Cytometric Separation of X and Y Chromosome-bearing Sperm Based on DNA Difference: a Review Reproduction Fertility and Development vol. 7, pp. 893-903 (1995).*
Pena et al. Antioxidant supplementation in vitro improves boar sperm motility and mitochondrial membrane potential after cryopreservation of different fractions of the ejaculate Animal Reproduction Science vol. 78 pp. 85-98 (2003).*
De Lara, Jocelyn, et. al. "Flourescent In Situ Hybridization of the Telomere Repeat Sequence in Hamster Sperm Nuclear Structures", *Journal of Cellular Biochemistry*, 53, p. 213-221 1993.
Garner, Dual L., Flow cytometric sexing of mammalian sperm, *Theriogeneology*, 65, (2006) p. 943-957.
Habermann, F.A., et. al, "Validation of sperm sexing in the cattle (*Bos taurus*) by dual colour fluorescence in situ hybridization", *J. Anim. Bree. Gente*, 122 (Suppl. 1) 2005, p. 22-27.
Johnson, Lawrence, et. al. "Preselection of sex of offspring in swine for production: current status of the process and its application", *Theriogeneology*,63 (2005) p. 615-624.
Perret, Jason et. al., "A Polymorphic Satellite Sequnce Maps to the Pericentric Region of the Bovine Y Chromosome", *Genimics*, 6, 1990, p. 482-490.
"Bovine Y-chromosome specific DNA probe, SEQ ID 1", Internet Citation, Feb. 14, 2006, p. 1, XP007910363, Accession No. AFG24798.
PCT Preliminary Report on Patentability Application No. PCT/EP2009/059117.

* cited by examiner

*Primary Examiner* — John S Brusca
(74) *Attorney, Agent, or Firm* — Greer, Burns & Crain Ltd.

(57) ABSTRACT

The present invention relates to a method and to compounds useable in the method for analysis of cells for the presence of an analyte and sorting the cells on the basis of the analyte. The compounds used in the method are optically detectable because of the content of a fluorochrome and contain a binder fraction which can specifically bind an analyte, in particular an oligonucleotide.

11 Claims, No Drawings

METHOD FOR CELL IDENTIFICATION AND CELL SORTING

The present invention relates to a method, and to compounds that can be used in the method, for analyzing cells for the presence of an analyte. The compounds used in the method for detecting an analyte are optically detectable and contain a binding portion that can specifically bind an analyte. Preferably, the binding portion is an oligonucleotide, also referred to as a nucleic acid sequence.

The use of detection conjugates in the method according to the present invention enables the detection of analytes, and in particular the identification and sorting or selection of cells on the basis of a specific analyte, using a detectable label contained in the detection conjugate. Correspondingly, the present invention also relates to the flow-cytometric analysis of cells, optionally with subsequent fractionation of the cells depending on the detected signal, e.g. by deflecting the cells into separate fractions or by thermal treatment of cells in dependence on the detected cell-specific signal; wherein preferably, for the detection and subsequent fractionation or treatment, the cells are spatially separated by spacing them in individual drops or in a continuous transport liquid.

STATE OF THE ART

WO 2008/060713 describes the sorting of cells using flow cytometry in which cells are labelled with nanoparticles bearing binding molecules that are specific for a cell type. Preferably, the nanoparticles consist of gold. The detection of bound nanoparticles takes place by determining the mass; preferably, the mass is determined as a change in the resonance frequency when the specific cell type binds to a specific functionalized wall of a resonator.

WO 2006/012597 describes methods for enriching X- or Y-chromosome containing sperms, infer alia by optical identification of the position of a species of sperm in a dispersion after specific labelling and heating of the positions in order to deactivate the labelled sperm.

WO 2006/012597 A2 also relates to the sex-specific labelling of sperms and to the deactivation of a labelled population by heating. DNA sequences for sex-specific labelling of sperm are not indicated.

WO 2007/095279 describes the specific labelling of leukemia-specific blood cells by magnetic enrichment, after the cells have been contacted with magnetic particles bearing a cell-type-specific oligonucleotide having a predetermined sequence.

DE 69905832 T2 claims a composition suitable for flow cytometry having a core consisting of a semiconductor nanocrystal with an outer layer that comprises a ligand, and a first part of a binding pair, which is linked to the core.

Medarova et al. (Nature Medicine 372-377 (2007)) describe magnetic nanoparticles that contain full-surface-bound siRNAs and myristyl-polyarginine peptides for penetration enhancement, in order to make the entrance of the siRNA into tumor cells visible in cancer cells, using nuclear resonance analysis.

DE 10 2005 044530 describes a method for sorting mammalian spermatozoa by dyeing DNA with a fluorescent dye, for example Hoechst Bisbenzimide H 33342, orienting the spermatozoa in an electrically conductive isotonic sheath liquid, making single the spermatozoa in drops of the sheath liquid, causing the drops to pass through the beam of an excitation laser, and measuring the relative fluorescence intensity of each spermatozoon, and separating the drops containing spermatozoa according to the measured fluorescence intensity. In order to increase the success of the sorting, the spermatozoa are immobilized by fluoride in the medium, which facilitates their orientation.

In the known methods for sorting spermatozoa it is disadvantageous that the spermatozoa must be oriented for the optical detection in order to enable measurement of the quantitative differences of the fluorescence signals for spermatozoa containing X-chromosomes versus spermatozoa containing Y-chromosomes.

OBJECT OF THE INVENTION

Therefore, regarding the known state of the art, the object of the invention is to provide an alternative method for the production of sex-chromosome-specific sperm fractions, as well as to provide materials that are useable for this production method and production methods for such materials.

GENERAL DESCRIPTION OF THE INVENTION

The invention achieves the aforementioned objects by providing detection conjugates that contain a sex-chromosome-specific nucleic acid sequence and a detectable label, and by providing a sorting method using the detection conjugates for the production of sex-chromosome-specific preparations or fractions. The sex-chromosome-specific nucleic acid sequence is preferably specific for the Y-chromosome, and is a single-strand RNA, DNA, or preferably PNA (peptide nucleic acid in which the (desoxy-) ribose-phosphate chain of DNA or RNA is replaced by a polypeptide that carries the bases, in particular replaced by N-(2-aminoethyl)-glycine units in peptide bonding.

In a first embodiment, the detectable label of the detection conjugate consists of a fluorochrome bound to the nucleic acid sequence, and a quencher bound to the nucleic acid at a distance from the fluorochrome. For example, the fluorochrome is situated at a first end of the sex-chromosome-specific nucleic acid sequence, and the quencher, which essentially absorbs the radiation emitted by the fluorochrome and emits it without radiation, is situated at the opposite, second end of the nucleic acid sequence, or in a second embodiment, consists of a metallic nanoparticle, preferably a gold nanoparticle, that is preferably bound directly to the nucleic acid sequence, i.e. without an additional coupling reagent. Therefore, this detection conjugate can consist of an oligonucleotide that is DNA, RNA, or PNA, a fluorochrome hound to the oligonucleotide, and a quencher bound to the oligonucleotide at a distance from the fluorochrome, the oligonucleotide being DNA, RNA, or PNA and having a sex-chromosome-specific nucleic acid sequence, or having an allele-specific or SNP-specific nucleic acid sequence.

In both embodiments of the invention, the sex-chromosome-specific dyeing and detection of spermatozoa takes place in that the sex-chromosome-specific nucleic acid sequence of the detection conjugate adsorbs onto the sex chromosome, and thereby changes the detectable signal of the label. In the first embodiment, a fluorescence signal can be radiated by the fluorochrome in a detectable way only if the detection conjugate hybridizes with the sex chromosome by means of its nucleic acid sequence, whereby the fluorochrome is separated from the quencher. In contrast to the hybridization to DNA of the target cell, the detection conjugate of the first embodiment, in the state in which it is not hybridized with a (sex) chromosome, is in a conformation such that the quencher is within the Förster radius of the fluorochrome and absorbs the radiation emitted by the fluorochrome and emits it essentially without radiation, for example by dissipation. Correspondingly, without specific hybridization a fluorescence signal of the detection conjugate of this embodiment is not detectable, or is detectable only to a significantly reduced degree.

For the purposes of the invention, reference to a nucleic acid sequence is to be understood as meaning an oligonucleotide, in particular in the form of PNA, preferably having a base sequence, in particular a sex-chromosome-specific base sequence, which is hybridizable with a predetermined genomic DNA segment of a target cell that is to be analyzed.

In the second embodiment, the surface plasmon resonance changes due to the sex-chromosome-specific hybridization of the nucleic acid sequence of the detection conjugate. Therefore, in this embodiment the detectable signal also changes in dependence on the sex-chromosome-specific hybridization of the nucleic acid sequence of the detection conjugate to the sex chromosome of the analyzed target cells, which are in particular gametes, particularly preferably spermatozoa.

In the second embodiment, the binding portion can be an antibody, natural or synthetic, single-chain or two-chain, preferably a nucleic acid sequence, for example RNA, DNA, preferably PNA, or a receptor-specific ligand or another compound that specifically interacts with a surface-hound component of a cell or with a cell-internal component, in particular an antibody. This detection conjugate can consist of an oligonucleotide bound to a metal nanoparticle, the oligonucleotide being DNA, RNA, or PNA and having a sex-chromosome-specific nucleic acid sequence or having an allele-specific or SNP-specific nucleic acid sequence.

The second embodiment of the present invention is also described with reference to detection conjugates that contain a nucleic acid sequence as a binding portion, preferably PNA: the nucleic acid sequence is here named as representative of other binding portions and may be replaced by other binding portions, in particular by antibodies. Correspondingly, with reference to the second embodiment, the nucleic acid sequence is used to represent other binding molecules in the detection conjugate, and the nucleic acid sequence can correspondingly be replaced by other binding molecules.

Surprisingly, the hybridization of the sex-chromosome-specific nucleic acid sequence of the detection conjugate is also possible with the highly condensed DNA that is present in spermatozoa. Such a hybridization could not be derived from the state of the art, because there intercalating dyes, in particular Hoechst Bisbenzimide 333425, are used that are smaller than the detection conjugate of the invention and that adsorb to DNA without sequence specificity. It is preferred that in the second embodiment the nanoparticles of the detection conjugate have bound penetration-enhancing compounds, for example polyarginine peptides, particularly preferably with a bound rest of myristic acid.

For the production of sex-chromosome-specific sperm fractions, in both embodiments of the invention the following method can be carried out:
Contacting of intact, viable gametes, in particular spermatozoa, obtained from a male non-human mammal, with a detection conjugate;
making single of the gametes, in particular spermatozoa, either in drops of a sheath liquid that is preferably electrically conductive and isotonic, or in a fluid stream that is produced for example in a flow cytometer;
excitation of the detection conjugate, e.g. by irradiation of radiation having an excitation wavelength, in the first embodiment in order to excite fluorescence, and in the second embodiment in order to excite the surface plasmon resonance;
detection of the signal emitted by the detection conjugate, in the first embodiment by measuring the fluorescence and in the second embodiment by measuring the emitted radiation of the surface plasmon resonance;
sorting of the gametes, in particular spermatozoa, corresponding to the measured signal intensity for production of at least two fractions, for example having a signal intensity on one side of a threshold value for the sex-chromosome-specific gamete fraction, in particular spermatozoa fraction, for whose sex chromosome the nucleic acid sequence of the detection conjugate was hybridizable or specific, and a fraction of gametes, in particular spermatozoa, for which signal intensities were measured on the other side of a threshold value, in which correspondingly the nucleic acid sequence of the detection conjugate does not hybridize.

A particular advantage of the method according to the invention is that when there is corresponding excitation the detection conjugates used each emit a detectable signal that has a significant qualitative deviation, said emission being specific for the sex chromosome contained in a gamete, in particular in a spermatozoon, and the signal significantly deviates depending on the hybridization, and this deviation being sufficiently large that it can be measured without a specific orientation of the spermatozoa relative to the irradiated excitation energy or relative to the detector receiving the emitted signal. For the purposes of the description, the term "spermatozoon" is used as a preferred example of a gamete.

Correspondingly, the method according to the invention for producing sex-chromosome-specific sperm fractions can preferably take place with individualizing of the spermatozoa during the detection of a signal from the detection conjugate and during the subsequent sorting into fractions on the basis of the measured detection signal, even without orientating spermatozoa along their longitudinal axis, e.g. in a flow cytometer with a continuous liquid phase.

Preferably, following the detection of the signal of the detection conjugate the individualized spermatozoa are assigned to a fraction, for example by deflection of drops or volume segments of the sheath liquid or carrier liquid containing the spermatozoa. The deflection can for example take place using an electrical field generated in dependence on the detected signal. In the alternative to this sorting into at least two fractions, it is also possible, after the detection, to leave the individualized spermatozoa uninfluenced in the carrier medium or sheath liquid, e.g. depending on the level of the detection signal, or, depending on the detection signal, to deactivate a proportion of the spermatozoa, for example by heating using targeted laser irradiation of the spermatozoa that, in the preceding detection, exceeded or fell below a signal threshold value. In this variant of both embodiments, a produced spermatozoa fraction contains the non-deactivated, that is for example non-irradiated spermatozoa, as well as deactivated (non-fertile) spermatozoa, wherein the deactivation depends on the falling below or exceeding of a threshold value for the measured detection signal. A corresponding flow cytometer can therefore have a laser that is set up for the deactivating irradiation of individual cells in the continuous liquid stream in dependence on the signal emitted by the detection conjugate.

Preferably, the spermatozoa are contacted with the detection conjugate in mixture with a penetration additive in order to facilitate the intake of the detection conjugate into the spermatozoa. Suitable penetration additives are transfection agents that can be used for animal cells, such as Fugene, Lipofectamine, oligofectamin, Optifect, DMRIE-C, penetratin 43-58, HIV I-Tat protein, Tat, peptide 49-59, Tat, peptide 48-62, Tat 2-4, Tat peptide (YGRKKRRQRRR- GYGRKKRRQRRRG), amphipathic peptides (MAPs), e.g. of the amino acid sequence KALA or KLAL, peptides containing cis-γ-amino-L-proline, VP22, Galparan, Transportan, MPG, SynB1, Fushi tarazu, Engrailed, pVEC, plsl, Hoechst 33342. Furthermore, the detection conjugates, in particular of the first embodiment, can be formulated as liposomes in order to enhance the penetration; in the second embodiment they are preferably formulated in mixture with liposomes.

A preferred nucleic acid sequence that is specific for the bovine Y-chromosome in particular is: 5' agc aca tct cgg tcc ctg 3' (SEQ ID NO. 1), ggc gac tgt gca agc aga (SEQ ID NO. 2), aga gac tgt gga acc gg (SEQ ID NO. 3), ggc gat tgt tca acc ag (SEQ ID NO. 4), and nucleic acid sequences complementary to each of these, and segments of 10 to 30, preferably 15 to 20 nucleotides having the sequence Y1.2, available at GenBank under accession number M26067, or the entire sequence Y1.2 and nucleic acid sequences complementary to each of these.

In the alternative to the sex-chromosome-specific nucleic acid sequence, a detection conjugate according to the invention can contain a nucleic acid sequence that is specific for an allele or an SNP (single-nucleotide polymorphism), in order to fractionate cells, in particular spermatozoa, allele-specifically or SNP-specifically.

Fluorochromes suitable for the first embodiment can be selected from the group consisting of Cy3, PE, FITC, APC, Alexa dyes, and Atto dyes, suitable quenchers can be selected from the group consisting of Dabcyl, Dabsyl, Dark-hole quencher, Black-Berry quencher, and QSY dyes.

In the second embodiment of the invention, it is preferred that the detection conjugates consist of colloidal gold nanoparticles having sex-chromosome-specific nucleic acid sequences bound directly thereto, optionally additionally having penetration-enhancing compounds bound directly to the gold nanoparticle. These detection conjugates therefore have the sex-chromosome-specific nucleic acid sequence in direct bonding to colloidal metal nanoparticles, in particular to colloidal gold nanoparticles, optionally additionally having penetration-enhancing agents bound directly to the nanoparticles.

For the excitation of the detection conjugates with colloidal gold nanoparticle, for example light having a wavelength of 450 to 600 nm, preferably 480 to 540 nm, particularly preferably approximately 520 nm, can be used for the irradiation. As a signal for the sex-chromosome-specific detection, the absorption of the excitation radiation is measured, wherein preferably the sex-chromosome-specific hybridization of the nucleic acid sequence of a detection conjugate is optionally detectable as a change in the absorption, by a shift of the wavelength, in particular to higher wavelengths.

Due to the detection of the radiation emitted by the detection conjugate, in the first embodiment as fluorescence and in the second embodiment as fluorescence, absorption, or a wavelength shift, both embodiments of the invention enable a sorting method for cells, in particular for spermatozoa, including the steps of contactless detection of the sex-chromosome-specific hybridization and subsequent fractionation and/or deactivation of individualized spermatozoa in dependence on the detected signal.

Preferably, in the first embodiment the nucleic acid sequence is bonded covalently to the fluorochrome and to the quencher, for example by an immediate chemical bond between the nucleic acid sequence and the fluorochrome and quencher, respectively. The chemical bond can be an amide bond, a thioether bond, or an ester bond.

The detection conjugates of the second embodiment are preferably colloidal gold nanoparticles that are conjugated with sex-chromosome-specific PNA in that nanoparticles are ablated from gold in an aqueous medium using an ultrashort pulse laser, and the nucleic acid sequence being present in the aqueous medium with the optional additional presence of a penetration-enhancing agent that is added simultaneously or later. The production of the gold nanoparticles by laser ablation using ultrashort pulses produces nanoparticles having a reactive surface that can also comprise partially oxidized Au+, Au3+ on the surface. Surprisingly, it was found that the production of metal nanoparticles by ultrashort pulse laser ablation in the presence of the sex-chromosome-specific nucleic acid sequence, as well as, optionally, the presence of penetration-enhancing agents present in mixture or added later, by itself brings about a direct bond of the nucleic acid sequence or of the penetration-enhancing agent to the gold nanoparticle. By the ultrashort pulse laser ablation, the metal particles, in particular gold nanoparticles, are partially oxidized and act as electron acceptors that form a bond with binding portions, in particular with nucleic acid sequences, and with penetration-enhancing agents that are optionally present at the same time or later, said bond being e.g. a complex bond or a coordinative bond.

In order to increase the binding strength, the nucleic acid sequences and the penetration-enhancing agent, respectively, can be provided with groups that are reactive with gold, in particular with thiol, carboxy, amide, and/or amine groups bearing the nucleic acid sequences at the 3' or 5' end for binding to a nanoparticle, preferably at the 3' end. It is possible to carry out this production method continuously in a flow chamber, wherein aqueous medium having a content of nucleic acid sequence is caused to flow over gold, while colloidal nanoparticles are being produced of the gold by irradiation with ultrashort pulse laser radiation. In this embodiment, penetration-enhancing agents can be used in mixture with nucleic acid sequences in a desired ratio, or penetration-enhancing agents can be added to the fluid stream downstream from the location of the production of the colloidal gold nanoparticles, so that after the reaction of the nanoparticles with nucleic acid sequences, reactive locations on the nanoparticles can react with penetration-enhancing agent.

Magnetic nanoparticles can be produced, e.g. gold nanoparticles, that then, as an aspect of the second embodiment, are detectable through detection of the shift of the relaxation when there is coupling to the specific sex chromosome, e.g. by detection of the relaxation difference due to the specific binding of the detection conjugate to or in mammalian spermatozoa, e.g. due to the relaxation difference between spermatozoa containing an X-chromosome and spermatozoa containing a Y-chromosome, with a sex-chromosome-specific nucleic acid sequence for the subsequent selection of the spermatozoa. Using an unspecific nucleic acid sequence of the detection conjugate, the detection and selection can take place on the basis of the quantitative relaxation difference, because spermatozoa also differ in their total DNA content.

As an alternative to the sex-chromosome-specific nucleic acid sequence, an arbitrary nucleic acid sequence, or a dye that binds unspecifically to DNA, e.g. Hoechst Bisbenzimide H33342, can be contained in the detection conjugates, so that for identification on the basis of the sex chromosome, a quantitative difference of the signal is detectable due to the lower total DNA content of the spermatozoa that contain a Y-chromosome.

The nanoparticles contained in detection conjugates according to the invention are preferably produced by ultrashort pulse laser ablation of a metal in an aqueous environment, e.g. immersed in an aqueous composition, the ultrashort pulse having a pulse duration of 10 fs to 15 ps at a wavelength of greater than 330 nm, maximally 1030 nm, in particular in the range from 500 to 1000 nm. The duration of the ablation is preferably approximately 10 to 200 s, e.g. 40 to 60 s, in particular 53 s, at a pulse energy of approximately 50 to 200 µJ, in particular 80 to 120 µJ, preferably 120 µJ, the pulse duration is approximately 100 to 140 fs, in particular approximately 120 fs, preferably at 800 nm.

This production method yields nanoparticles that, even with the bound binding portion, which is for example a peptide or a sex-chromosome-specific nucleic acid sequence, preferably as PNA, have a size and/or conformation that is particularly suitable for penetration of the cell wall of mammalian spermatozoa, in particular of the bovine. The nanoparticles have for example a size of 1 to 150 nm, to 100 nm, preferably 5 to 50 nm or to 25 nm.

Due to the production of nanoparticles using ultrashort pulse laser radiation, the method for producing detection conjugates containing nanoparticles produces detection conjugates having a particularly small nanoparticle size, because the nanoparticles produced within a very short time span, e.g. 1 to 10 ps have a very small size, in which a high reactivity of the gold nanoparticle is present, for example with nucleic acid sequences containing thiol, while the agglomeration of the nanoparticles begins subsequent to this time span. Correspondingly, the nucleic acid sequences that are to be used for the production method preferably have thiol, keto, carboxy, amide, or amine groups, in order to produce a corresponding coordinative bond to the nanoparticle, i.e. without use of an additional coupling reagent between the nucleic acid sequence and the nanoparticle.

The non-human sperm preferably originates from even-toed ungulates or from odd-toed ungulates, in particular from the bovine, swine, sheep, camel, or horse.

DETAILED DESCRIPTION OF THE INVENTION

The invention is now described in more detail by way of examples.

Example 1

Production of a Detection Conjugate

In correspondence to the first embodiment of the invention, a detection conjugate was bound via covalent bonding of a fluorochrome, for example Cy3, PE, FITC, APC, an Alexa dye, or an Atto dye, to the 5' end of a nucleic acid sequence that is specific for the Y-chromosome, and to the 3' end of the nucleic acid sequence a quencher that is suitable for absorption from the fluorochrome, Dabcyl, Dabsyl, Dark-Hole quencher, Black-Berry quencher, or a QSY dye was bound. The nucleic acid sequence was a PNA oligonucleotide having the sequence: 5' age aca tct egg tee ctg 3'.

Example 2

Production of a Detection Conjugate Having Gold Nanoparticles

For production of a detection conjugate having a metallic nanoparticle, gold foil was introduced into an aqueous solution containing the nucleic acid sequence used in Example 1. The gold foil was irradiated with 120 fs laser pulses at a wavelength of 800 nm at a maximum energy of 400 µJ per pulse, with beam diameter 4 mm at a distance of approximately 40 mm from the lens to the gold foil, at a repetition rate of 5 kHz. The energy applied to the gold foil was approximately 100 µJ. The aqueous solution contained approximately 3 µM nucleic acid sequence in water, with a layer height of approximately 1 cm above the gold foil.

The analysis of the reaction products by polyacrylamide gel electrophoresis showed only a slight degradation of the nucleic acid sequence. Analysis of the reaction products by transmission electron microscopy showed that the conjugates had a size distribution having an average of approximately 5.2 to 5.5 nm. The conjugates were not agglomerated, and had an approximately spherical shape; with the parameters used, approximately 20 µg/min gold particles were produced, which formed a stable bond with the nucleic acid sequence without additional chemical coupling reagents.

Example 3

Detection of Sperm Containing Y-Chromosomes in Fresh Semen, and Sex-Specific Sorting Thereof Freshly obtained bull semen was thinned in thinner in standard fashion, and was incubated with detection conjugate produced according to Example 1 or Example 2 for 30 to 60 minutes at a temperature of 20° C. to 40° C., and was subsequently irradiated in a flow cytometer according to U.S. Pat. No. 5,125,759 or DE 10 2005 044 530 with light having the respective excitation wavelength for the fluorochrome, or 520 nm for the gold nanoparticles. The emission was measured in each case.

For the spermatozoa containing Y-chromosomes specifically labelled with detection conjugate according to Example 1, a fluorescence signal was measured, whereas the spermatozoa containing X-chromosomes did not emit a fluorescence signal. This shows that this detection conjugate produces a detectable signal when irradiated at the excitation wavelength only if there is hybridization of the nucleic acid sequence, while cells that do not contain nucleic acid that hybridizes with the nucleic acid sequence of the detection conjugate upon irradiation emit no fluorescence signal, or only a negligible one. For the spermatozoa dyed in chromosome-specific fashion with detection conjugate according to Example 2, a change in the detected surface plasmon resonance was determined for the spermatozoa containing an Y-chromosome, while the spermatozoa containing an X-chromosome showed a surface plasmon resonance that was changed significantly less.

Depending on the detected signal, the spermatozoa were deflected into sex-chromosome-specific fractions using an electrical field.

As an alternative to the use of a flow cytometer, i.e. without orienting the spermatozoa in a particular position relative to the longitudinal axis, the detection and sorting method could also be carried out in a conventional flow cytometer having a device for signal-dependent cell sorting (BD Bioscience, FACScalibur, or FACSAria).

Optionally, a fluoride was added in order to immobilize the spermatozoa, e.g. added to the sheath liquid or transport liquid used during the sorting method, and/or prior to or during the addition of the detection conjugate, in order to increase the penetration of the detection conjugate into the spermatozoa. Fluoride ions were added in the range from 0.1 to 100 mM, preferably 10 nM to 10 mM. It was found that the optimal concentration of the fluoride, e.g. NaF or KF, varied between different species and between individuals. The optimal concentration for the species is specific and could be determined generally as the concentration that, under microscopic inspection, resulted in immobilization of at least 90% of the spermatozoa, and preferably of essentially all the spermatozoa. Correspondingly, the present invention also relates to compositions of the sperm fractions produced using the method of the present invention, and to methods for producing sex-specific sperm fractions with subsequent preservation of the sperm fractions of nonhuman mammals, in each case preferably in the presence of fluoride and/or antioxidation agents.

The invention claimed is:

1. A method for producing a fraction of nonhuman mammalian gametes, the method comprising:
   contacting intact viable nonhuman mammalian gametes with a detection conjugate, wherein the gametes are spermatozoa and wherein the detection conjugate has an oligonucleotide having a sex-chromosome-specific nucleic acid sequence that is bound to a gold nanoparticle;
   irradiating the detection conjugate with radiation having an excitation wavelength;
   detecting radiation emitted by the detection conjugate when irradiated with the radiation having an excitation wavelength by measuring the emitted radiation of the surface plasmon resonance; and
   deflecting the spermatozoa into one of at least two fractions of viable nonhuman gametes in dependence on a measured signal, wherein one of the at least two fractions has a predominant portion of fertile gametes containing an X-chromosome or a Y-chromosome.

2. The method according to claim 1, wherein the sex-chromosome-specific nucleic acid sequence is bound directly to the gold nanoparticle.

3. The method according to claim 1, wherein the gold nanoparticle has a size of from 1 to 100 nm.

4. The method according to claim 1, wherein the oligonucleotide is PNA.

5. The method according to claim 1, wherein the nucleic acid sequence has the base sequence 5' agc aca tct cgg tcc ctg 3' (SEQ ID NO. 1) or a base sequence complementary thereto.

6. The method according to claim 1, wherein the fraction of nonhuman mammalian gametes is intact and viable.

7. The method according claim 1, wherein the mammalian gametes contain fluoride and/or antioxidation agent.

8. A method for producing a fraction of nonhuman mammalian gametes, the method comprising:
   contacting intact viable nonhuman mammalian gametes with a detection conjugate;
   irradiating the detection conjugate with radiation having an excitation wavelength, wherein the detection conjugate has an oligonucleotide having a sex-chromosome-specific nucleic acid sequence that is bound directly to a gold nanoparticle;
   detecting radiation emitted by the detection conjugate when irradiated with the radiation having an excitation wavelength by measuring the emitted radiation of the surface plasmon resonance;
   heat-treating the gametes by targeted laser radiation in dependence on a detected signal; and
   obtaining a fraction of nonhuman mammalian gametes having a predominant portion of fertile gametes containing an X-chromosome or a Y-chromosome.

9. A method for producing a fraction of nonhuman mammalian gametes, the method comprising:
   producing a detection conjugate having an oligonucleotide having a sex-chromosome-specific nucleic acid sequence that is bound directly to a gold nanoparticle, wherein producing the detection conjugate includes the production of gold nanoparticles by ultrashort pulse laser ablation of gold in a liquid that contains the nucleic acid sequence;
   contacting intact viable gametes with the detection conjugate;
   irradiating the detection conjugate with radiation having an excitation wavelength;
   detecting radiation emitted by the detection conjugate when irradiated with the radiation having an excitation wavelength by measuring the emitted radiation of the surface plasmon resonance, and
   obtaining a fraction of nonhuman mammalian gametes having a predominant portion of fertile gametes containing an X-chromosome or a Y-chromosome.

10. The method according to claim 9, wherein the ultrashort laser pulse has a pulse duration of 10 fs to 15 ps at a wavelength of at least 330 nm up to maximally 1030 nm.

11. The method according to claim 9, wherein the ablation time is 10 to 200 s at a pulse energy of 50 to 200 µJ and a pulse duration of 100 to 140 fs at 800 nm.

\* \* \* \* \*

UNITED STATES PATENT AND TRADEMARK OFFICE
CERTIFICATE OF CORRECTION

PATENT NO.       : 8,649,983 B2                                    Page 1 of 1
APPLICATION NO.  : 13/003962
DATED            : February 11, 2014
INVENTOR(S)      : Rath et al.

It is certified that error appears in the above-identified patent and that said Letters Patent is hereby corrected as shown below:

In the Specification:

| | |
|---|---|
| Col. 1, line 36 | Please delete "infer" and insert --inter-- therefor. |
| Col. 2, line 29 | After "acid", please insert --)--. |
| Col. 2, line 41 | Between "or" and "in", please insert --,--. |
| Col. 2, line 47 | Please delete "hound" and insert --bound-- therefor. |
| Col. 3, line 24 | Please delete "surface-hound" and insert --surface-bound-- therefor. |
| Col. 4, line 65 | After "DMRIE-C," please insert --AntHD,--. |
| Col. 5, line 56 | After "steps of", please insert --:--. |
| Col. 6, line 58 | Please delete "unspecitically" and insert --unspecificially-- therefor. |
| Col. 7, line 54 | Please delete "age" and insert --agc-- therefor. |
| Col. 7, line 54 | Please delete "egg" and insert --cgg-- therefor. |
| Col. 7, line 54 | Please delete "tee" and insert --tcc-- therefor. |

Signed and Sealed this
Seventh Day of October, 2014

Michelle K. Lee
*Deputy Director of the United States Patent and Trademark Office*

```
                        SEQUENCE LISTING

<160> NUMBER OF SEQ ID NOS: 4

<210> SEQ ID NO 1
<211> LENGTH: 18
<212> TYPE: DNA
<213> ORGANISM: artificial sequence
<220> FEATURE:
<223> OTHER INFORMATION: SEQ ID NO: 1: Y-chromosome-specific
      oligonucleotide

<400> SEQUENCE: 1
agcacatctc ggtccctg                                                 18

<210> SEQ ID NO 2
<211> LENGTH: 18
<212> TYPE: DNA
<213> ORGANISM: artificial sequence
<220> FEATURE:
<223> OTHER INFORMATION: SEQ ID NO: 2: Y-chromosome-specific
      oligonucleotide

<400> SEQUENCE: 2
ggcgactgtg caagcaga                                                 18

<210> SEQ ID NO 3
<211> LENGTH: 17
<212> TYPE: DNA
<213> ORGANISM: artificial sequence
<220> FEATURE:
<223> OTHER INFORMATION: SEQ ID NO: 3: Y-chromosome-specific
      oligonucleotide

<400> SEQUENCE: 3
agagactgtg gaaccgg                                                  17

<210> SEQ ID NO 4
<211> LENGTH: 17
<212> TYPE: DNA
<213> ORGANISM: artificial sequence
<220> FEATURE:
<223> OTHER INFORMATION: SEQ ID NO: 4: Y-chromosome-specific
      oligonucleotide

<400> SEQUENCE: 4
ggcgattgtt caaccag                                                  17
```